United States Patent [19]

Diener

[11] Patent Number: 4,820,043

[45] Date of Patent: Apr. 11, 1989

[54] TECHNOSCOPE FOR DETERMINING THE EXTENT OF DAMAGE TO AN OBJECT

[75] Inventor: Jörg Diener, Oberderdingen, Fed. Rep. of Germany

[73] Assignee: Richard Wolf, GmbH, Knittlingen, Fed. Rep. of Germany

[21] Appl. No.: 164,831

[22] Filed: Mar. 7, 1988

[30] Foreign Application Priority Data

Mar. 5, 1987 [DE] Fed. Rep. of Germany ....... 3707073

[51] Int. Cl.$^4$ .................... G01B 11/02; G02B 23/26
[52] U.S. Cl. .................... 356/241; 356/383; 128/6
[58] Field of Search ............ 356/241, 383, 384, 397; 128/4, 6

[56] References Cited

U.S. PATENT DOCUMENTS 4,078,864  3/1978  Howell ..................... 356/241 X

Primary Examiner—Vincent P. McGraw
Attorney, Agent, or Firm—Hill, Van Santen, Steadman & Simpson

[57] ABSTRACT

A technoscope for determining the extent of damage to objects includes an endoscope which is displaceable with a fixed stroke in a guide with a point of the object being coincided with a scale at both terminal positions of the stroke, the scale being in the form of a transparent screen plate which is displaceable transversely of the axis of the endoscope, a first measurement value transmitter for mechanically detecting the displacement value of the endoscope and for converting the same into an electrical signal being connected to a calculator, and a distal prism for lateral viewing being pivotally displaceable in the endoscope with the angle of pivotal displacement being mechanically detected and converted into an electrical signal which is transmitted to the calculator.

2 Claims, 2 Drawing Sheets

4,820,043

TECHNOSCOPE FOR DETERMINING THE EXTENT OF DAMAGE TO AN OBJECT

BACKGROUND OF THE INVENTION

1. Field of the Invention

The invention relates to a technoscope for determining the extent of damage to an object, of the kind in which an endoscope provided with a proximal ocular and a distal prism for lateral viewing is displaceable axially by a fixed stroke in a guide which is immobilised with respect to the object, and a point of the object is depicted on a scale observable through the ocular in both terminal positions of the endoscope stroke.

2. Description of the Prior Art

Technoscopes of the aforesaid kind have been disclosed in DE-OS No. 35 12 602 in which a quantitative determination of damage in a technical object is obtained by means of an endoscope. In this technoscope, an endoscope having a distal lateral objective and intended to be secured at a particular distance from the point of damage with respect to the object, is mounted in a guide shaft, in which it is displaceable by a particular axial stroke into two terminal positions. A point of the damage to the object is aimed at right angles to the longitudinal axis in the one terminal position, whereupon the endoscope is displaced into the other terminal position, so that the initially sighted point moves on a scale in the endoscope, so that the number of scale graduations then determines the angle of observation. Because of the constant distance of the objective from the damaged area to the aforesaid angle and the axial stroke of the enndoscope, the extent of the damaged area may be determined by calculation. Since the values do not however yield any direct indication of the actual dimensions, it is absolutely necessary to determine these from a list with recourse to the known values. This method is very onerous, timeconsuming and subject to errors.

Accordingly, the main object of the present invention is to determine quantitative measured of damage to technical objects, e.g. power plants, precisely and immediately without difficulty without having to perform lengthy and erroneous calculations and without having to utilise technically complex technoscopes.

SUMMARY OF THE INVENTION

To this end the present invention consists in a technoscope for determining the extent of damage to an object and including an endoscope having a proximal ocular, a distal prism for lateral viewing, and being displaceable axially by a fixed stroke in a guide which can be fixed with respect to the object, a scale in the form of a transparent screen plate for coinciding with a point of the object and being observable through the ocular in both terminal positions of the endoscope stroke, the transparent screen plate being displaceable transversely of the endoscope axis by means of a micrometer screw which is operable from outside the endoscope, a first measurement value transmitter for mechanically detecting the displacement value of the endoscope and for converting the said displacement value into an electrical signal which is fed to a calculator to calculate the object distance, means for pivotally displacing said distal prism, and a second measurement value transmitter for mechanically detecting the pivotal displacement value of said distal prism and for converting the pivotal displacement value into an electrical signal which is fed to the calculator to calculate the extent of the damage.

BRIEF DESCRIPTION OF THE DRAWINGS

In order that the invention may be more readily understood, an embodiment thereof will now be described, by way of example, with reference to the accompanying drawings, in which.

DESCRIPTION OF THE PREFERRED EMBODIMENT

Figure 1:
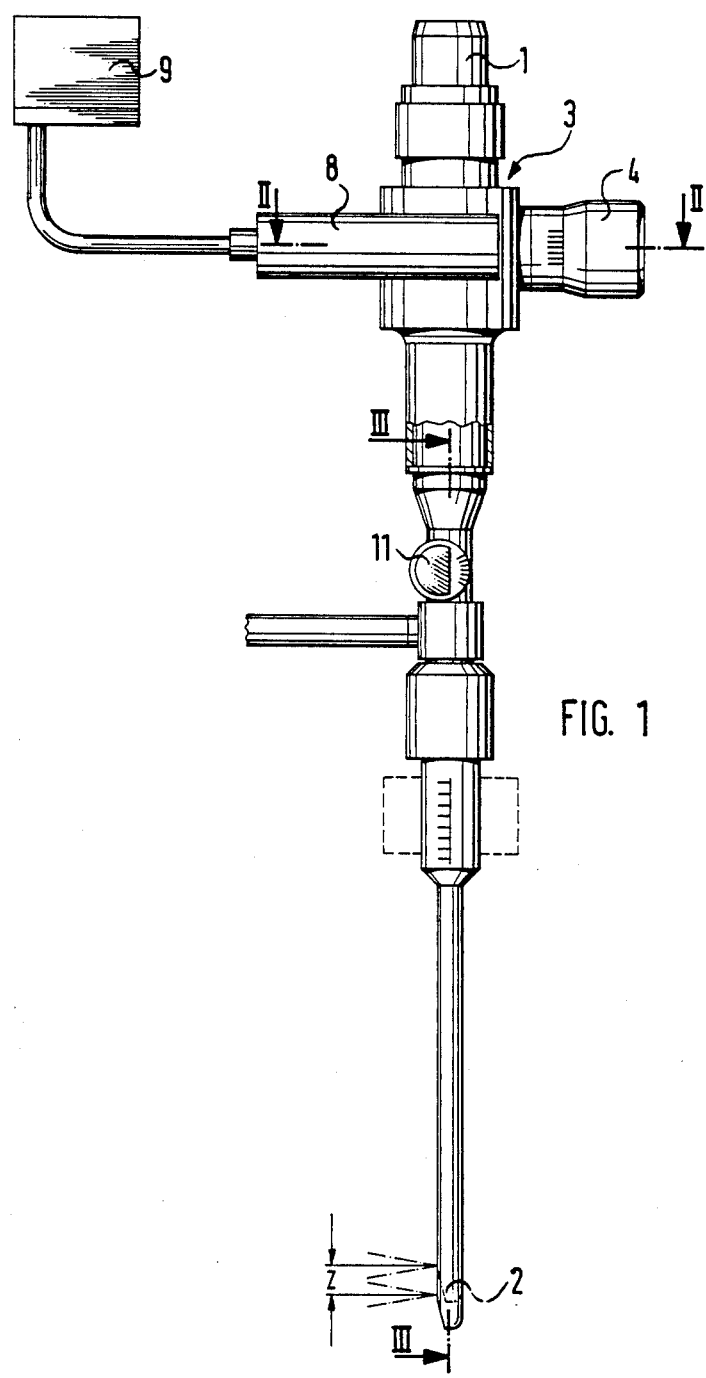
FIG. 1 is a plan view of a technoscope for determining the extent of damage to an object.
Figure 3:
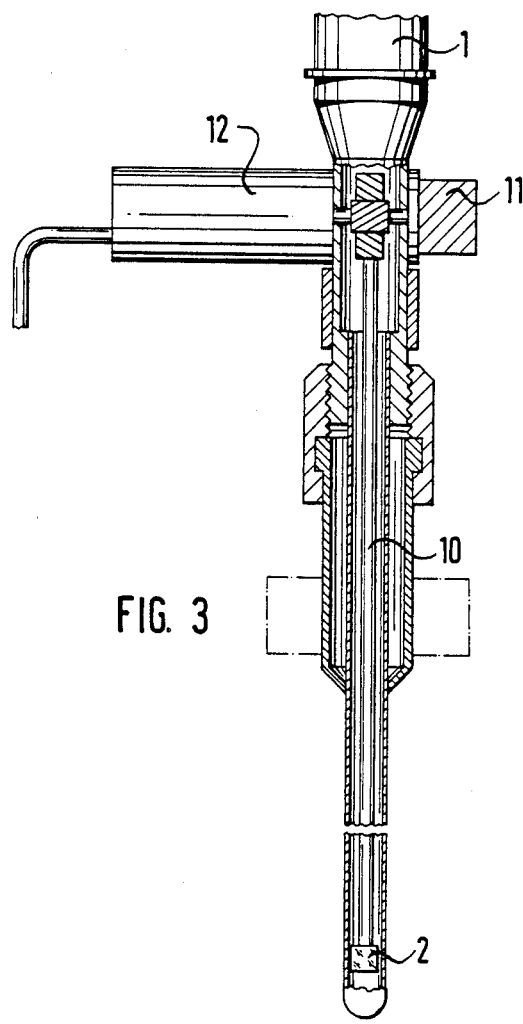
FIG. 3 is an axial cross-section taken along the line III—III of FIG. 1.
Figure 2:
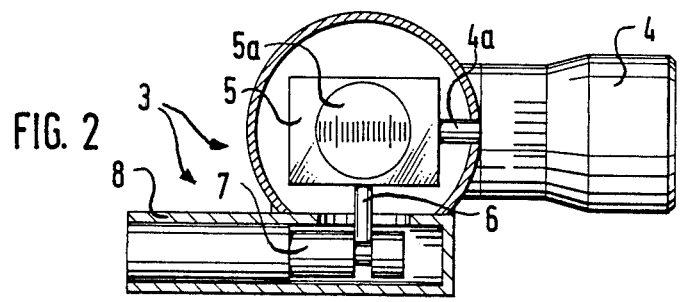
FIG. 2 is a cross-section taken along the line II—II of FIG. 1.

Referring to the drawings, there is shown a technoscope comprising an endoscope having a proximal ocular 1 and a distal prism 2 for lateral viewing. The endoscope is mounted for utilisation in a guide which is fixed with respect to an object, e.g. a power plant which is to be examined under illumination from a light source through a lighting connection and is axially displaceable by a fixed stroke in the guide, as disclosed in the DE-OS No. 35 12 602.

The ocular 1 forms part of a measuring attachment 3 in which a micrometer measuring attachment 3 in which a micrometer screw 4a, having a handle 4 is rotatably mounted and extends transversely of the endoscope axis. The micrometer screw 4a acts on a transparent screen plate 5 having a graduated scale 5a. The screen plate 5 is connected, e.g. by a pin 6, to a displacing element 7 of a measurement value transmitter 8 by means of which the mechanical displacement value is converted into a corresponding electrical signal. An evaluator unit and a calculator 9 are connected to the measurement value transmitter 8 which feeds the electrical signal thereto.

The prism 2 for lateral viewing is mounted for pivotable displacement in the endoscope by means of a turning handle 11 via a mechanical connection 10 which constitute a setting mechanism. The angle of pivotal displacement of the prism 2 is picked up mechanically by a measurement value transmitter 12 and converted into a corresponding electrical signal which is also fed to the evaluator unit and the calculator 9.

To determine the extent of damage to a technical object, a point of damage, e.g. the start of a fissure is observed by means of the ocular 1 in the one terminal position of the fixed stroke Z (FIG. 1) of the endoscope, and whilst doing so is placed in coincidence with a scale graduation of the scale 5a of the screen plate 5. The endoscope is thereupon displaced axially in the fixed guide by the stroke Z whilst the image of the damage point observed is displaced over the graduated scale 5a. The screen plate 5 is then displaced by operation of the handle 4 until the image of the damage point coincides again with the originally set graduation of the scale 5a. The aforesaid displacement of the screen plate 5 is detected mechanically by the measurement value transmitter 8, converted into a corresponding electrical signal and fed to the evaluator unit and calculator 9. The object distance is thereupon calculated initially by trigonmetrical calculations based on the known and established values, the same representing the measure for determining the scale reproduction factor.

To determine the length of the damage or length of the fissure in the object, the screen graduation initially selected and determined is then adjusted by displacement of the screen plate 5 by means of the handle 4 at one extremity of the damage, e.g. the extremity of a fissure. This displacement value is detected by the measurement value transmitter 8, converted into an electrical signal and fed to the evaluator unit and the calculator 9. If the damage which is to be measured is situated in a sighting direction deviating from a plane at right angles to the endoscope axis, the prism 2 may be pivoted at an angle to the longitudinal axis by means of the handle 11. The angle of pivotal displacement is then detected by the second measurement value transmitter 12 and converted into an electrical signal which is also fed to the evaluator unit and calculator 9.

The calculation of the extent of the damage, e.g. the length of a fissure or crack, will then occur by means of the calculator 9 on the basis of the values determined under application of the calculated reproduction factor and will subsequently be reproduced as a numerical value on a display unit (not shown).

In conclusion, it should be stated that the evaluator unit receives a start and stop signal respectively in each case at the start and end of each actuation of the handles 4 and 11, by manual infeed, for unequivocal definition of momentary measurement - the start and finish. After completion of the measuring operation, the calculator should be started by means of a supplemental signal which is to be fed in manually, for calculation of the extent of the damage.

It should be appreciated that the invention is not limited to the particular embodiment described but includes all modifications and variations falling within its scope.

What is claimed is:

1. In a technoscope for determining the extent of damage to an object and including an endoscope having a proximal ocular, a distal prism for lateral viewing, and being displaceable axially by a fixed stroke in a guide which can be fixed with respect to the object, and a scale for coinciding with a point of the object and being observable through the ocular in both terminal positions of the endoscope stroke, the improvement which comprises:

a transparent screen plate which incorporates said scale and which is displaceable transversely of the endoscope axis by means of a micrometer screw which is operable from outside the endoscope, a first measurement value transmitter for mechanically detecting the displacement value of the endoscope and for converting the said displacement value into an electrical signal which is fed to a calculator to calculate the object distance, means for pivotally displacing said distal prism, and a second measurement value transmitter for mechanically detecting the pivotal displacement value of said distal prism and for converting the pivotal displacement value into an electrical signal which is fed to the calculator to calculate the extent of the damage.

2. A technoscope as claimed in claim 1, wherein the calculator includes an evaluator unit through which the electrical signals are fed.

* * * * *